:::

(12) United States Patent
Lichtenberg et al.

(10) Patent No.: US 9,267,103 B2
(45) Date of Patent: Feb. 23, 2016

(54) COMPLIANT MULTI-WELL PLATE (75) Inventors: Jan Lichtenberg, Unterengstringen (CH); Wolfgang Moritz, Bassersdorf (CH); Jens Kelm, Zürich (CH)

(73) Assignee: INSPHERO AG, Schlieren (CH)

( * ) Notice: Subject to any disclaimer, the term of this patent is extended or adjusted under 35 U.S.C. 154(b) by 0 days.

(21) Appl. No.: 13/810,984

(22) PCT Filed: Jul. 27, 2011

(86) PCT No.: PCT/IB2011/001735
§ 371 (c)(1),
(2), (4) Date: May 22, 2013

(87) PCT Pub. No.: WO2012/014047
PCT Pub. Date: Feb. 2, 2012

(65) Prior Publication Data
US 2013/0236924 A1 Sep. 12, 2013

Related U.S. Application Data (60) Provisional application No. 61/367,993, filed on Jul. 27, 2010.

(51) Int. Cl.
*C12M 1/12* (2006.01)
*B01L 3/00* (2006.01)
(Continued)

(52) U.S. Cl.
CPC .............. *C12M 41/46* (2013.01); *B01L 3/5088* (2013.01); *B01L 3/50855* (2013.01); *B29C 45/1676* (2013.01); *C12M 23/12* (2013.01); *C12M 23/26* (2013.01); *C12M 23/38* (2013.01); *C12M 25/01* (2013.01); *C12M 29/00* (2013.01); *B01L 3/505* (2013.01); *B01L 2200/0642* (2013.01); *B01L 2200/143* (2013.01); *B01L 2300/0829* (2013.01); *B01L 2300/123* (2013.01)

(58) Field of Classification Search
CPC .. B01L 3/50855; B01L 3/5088; C12M 41/46; C12M 23/12; C12M 23/26; C12M 23/38; C12M 25/01; C12M 29/00; B29C 45/1676
See application file for complete search history.

(56) References Cited

U.S. PATENT DOCUMENTS 4,657,867 A 4/1987 Guhl et al.
5,587,321 A 12/1996 Smith et al.
(Continued)

FOREIGN PATENT DOCUMENTS

JP 55-039029 A 3/1980
JP 55-59350 U 4/1980
(Continued)

OTHER PUBLICATIONS

International Search Report dated Dec. 28, 2011.
(Continued)

*Primary Examiner* — Gautam Prakash
(74) *Attorney, Agent, or Firm* — Kratz, Quintos & Hanson, LLP (57) ABSTRACT

Multi-well plate (1) comprising a plurality of wells (4), a frame (5) for holding the plurality of wells (4) in a defined arrangement, a support element (50) for contacting a surface when the multi-well plate (1) is placed on the surface, wherein at least one well (4) of the plurality of wells is elastically displaceable relative to said support element (50).

14 Claims, 11 Drawing Sheets

(51) Int. Cl.
*C12M 1/32* (2006.01)
*C12M 1/00* (2006.01)
*B29C 45/16* (2006.01)
*C12M 1/34* (2006.01)

(56) References Cited

U.S. PATENT DOCUMENTS

| | | | |
|---|---|---|---|
| 7,208,125 | B1 | 4/2007 | Dong |
| 2003/0150379 | A1 | 8/2003 | Goodwin, Jr. |
| 2003/0235519 | A1* | 12/2003 | Sha et al. .................. 422/102 |
| 2007/0231214 | A1 | 10/2007 | Sakaguchi |
| 2008/0220481 | A1* | 9/2008 | Mortillaro et al. .......... 435/91.2 |

FOREIGN PATENT DOCUMENTS

| | | |
|---|---|---|
| JP | 61-167549 U | 10/1986 |
| JP | 62-59135 U | 4/1987 |
| JP | 09-325153 A | 12/1997 |
| JP | 11-295321 A | 10/1999 |
| JP | 2001-327874 A | 11/2001 |
| JP | 2006-514580 A | 5/2006 |
| JP | 2007-292737 A | 11/2007 |
| JP | 2008-008789 A | 1/2008 |
| WO | 2004/070090 A2 | 8/2004 |
| WO | 2010/031194 A1 | 3/2010 |
| WO | WO 2010/031194 A1 | 3/2010 |
| WO | 2010/049108 A1 | 5/2010 |
| WO | WO 2010/049108 A1 | 5/2010 |

OTHER PUBLICATIONS

Japanese of Action, for the Corresponding JP Application No. 2013-521239, mailed on Apr. 28, 2015, English translation only.
First Office Action, for the Corresponding CN Application No. 2011800370709, mailed on Jun. 16, 2014.
Second Office Action, for the Corresponding CN Application No. 2011800370709, mailed on Apr. 3, 2015.

* cited by examiner

|  | - elastic Element (-eE) | | + elastic Element (+eE) | |
|---|---|---|---|---|
|  | Volumen [μL] | Standard Error | Volume [μL] | Standard Error |
| 40 μL Dispensing | 38.43 | 1.84 | 39.02 | 0.32 |
| 20 μL Dispensing | 21.35 | 2.68 | 20.60 | 0.32 |
| 20 μL Aspirating | 14.47 | 2.68 | 17.88 | 0.20 |

Figure 13

| Production | Technology | Diameter [µm] (mean ± SD) | SD [%] |
|---|---|---|---|
| manual | conventional | 188,8 ± 21.0 | 11,1 |
| manual | hanging-drop with elastic elements | 174,1 ± 17,0 | 9,7 |
| automated | hanging-drop with elastic elements | 199,2 ± 6,7 | 3,4 |

– – manual_conventional      - - - - manual_hanging-drop
——— automated_hanging-drop

| manual production | manual production | automated production |
|---|---|---|
| conventional technology | hanging-drop technology with elastic elements ||

Figure 14

COMPLIANT MULTI-WELL PLATE

THE FIELD OF THE INVENTION

The present invention relates to a multi-well plate. The present invention relates in particular to a hanging-drop multi-well plate allowing for a reliable and precise loading of wells.

Multi-well plates have become a routine tool in research and development for biochemical analysis and cell-based assays. Technologies using cell-based assays are primarily based on monolayer cell cultures grown in multi-well plates with up to 1536 wells.

However, the biological relevance of monolayer cultures is only limited. The lack of an appropriate tissue-like three-dimensional (3D) environment and controlled co-culture modalities prevents native cell phenotype and functionality (Abbott, Nature 2003 (21) 870-2; Griffith and Swartz, Nat Rev Mol Cell Biol. 2006 (7) 211-24; Yamada and Cukierman, Cell. 2007 (130) 601-10). The use of organotypic cell-culture models with a superior biological relevance improves the predictivity compared to monolayer systems (Justice et al., Drug Discov Today 2009 (1-2) 102-7). However, the development of a mid- to high-throughput compatible technology for the generation of organotypic tissues is demanding.

The hanging drop plate for microtissue production disclosed in the PCT application published under number WO 2010/031194 has been developed for direct substitution of standard multi-well plates without requiring additional materials or processing steps. The well design of the hanging drop plate disclosed in WO 2010/031194 enables the generation of hanging drops by top loading in a 96-well or 384-well plate. A drawback of this plate design comprising an inlet and a culture compartment which are connected by a vertical microchannel, is that it requires direct contact of the pipette tips onto the surface of the individual wells during loading, leading to distortion of the pipette tips and inaccuracy in liquid handling in case of even light misalignment of the wells and/or of the pipettes, thus leading to significant variations in the volume of liquid loaded in each well. For current high-sensitive assay technologies precise volume control is mandatory to gain significant results.

SUMMARY OF THE INVENTION

An object of the present invention is thus to provide a multi-well plate in particular a hanging-drop multi-well plate which does not imply the above-mentioned problems.

An object of the invention is in particular to provide a multi-well plate in particular a hanging-drop multi-well plate that allows for a precise control of the quantity of liquid loaded in the wells.

These objects are achieved by a multi-well plate comprising a plurality of wells, a frame holding the plurality of wells in a defined arrangement, a support element for contacting a surface when the multi-well plate is placed on the surface, wherein at least one well of the plurality of wells is elastically displaceable relative to said support element.

Said elastic displacement of, according to variant embodiments of the invention, at least one well, a subset of wells, all wells or the frame, of the multi-well plate enables to account for variances in vertical and horizontal positions of pipette tips of single channel or multi-channel heads which have to be placed precisely on the well surface at a specific spatial position.

The multi-well plate of the present invention can be used for culturing cells or tissue, for performing assays or for performing protein crystallization.

The multi-well plate of the present invention is now described in more detail on the basis of selected, exemplary embodiments that are depicted in schematic drawings, which shall illustrate preferred embodiments without delimiting the scope of the present invention.

BRIEF DESCRIPTION OF THE FIGURES

FIG. 6b is a cut view of the multi-well plate of FIG. 6a.

DETAILED DESCRIPTION OF THE INVENTION

A well is understood herein to include culture wells, i.e. wells which can be used to culture or process cells, preferably animal cells, more preferably human cells. The wells are preferably culture wells. A subset of wells is understood herein to include a multi-well stripe, for example an 8-well stripe, a multi-well matrix, for example an 8×12 well matrix, and/or at least two individual wells. A subset of wells is preferably an 8-well stripe.

Flexible material or flexible element or flexible interconnection is understood herein to refer to a material or an element or an interconnection which has elastic properties.

Non limiting examples of flexible materials are: polydimethylsiloxane, silicone or other rubber-like materials.

Figure 1:
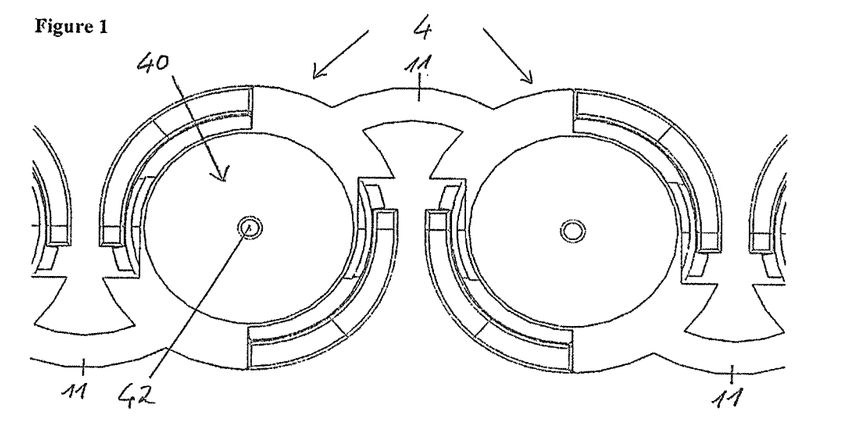
FIG. 1 is a top view of wells with springs and an elastic interconnection element, according to a preferred embodiment of the invention.
Figure 2:
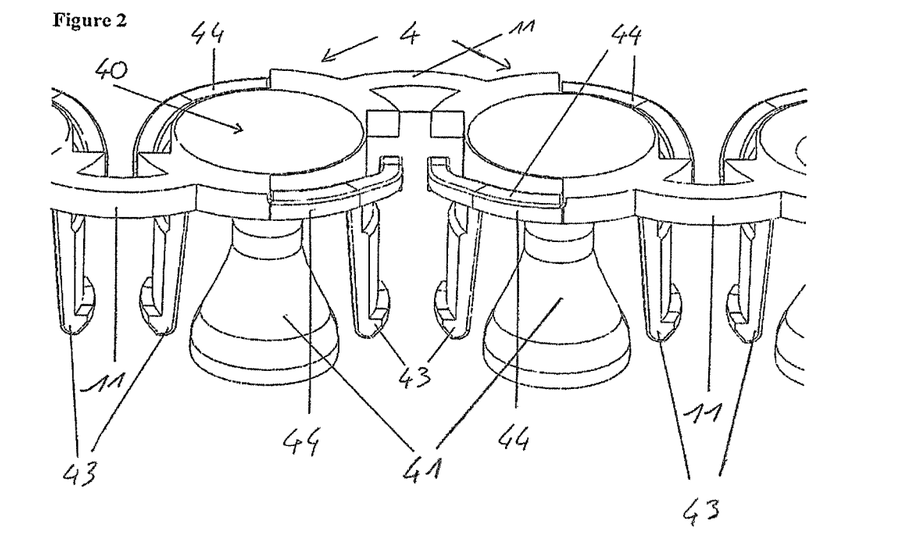
FIG. 2 is a perspective view of the wells of FIG. 1.
Figure 3:
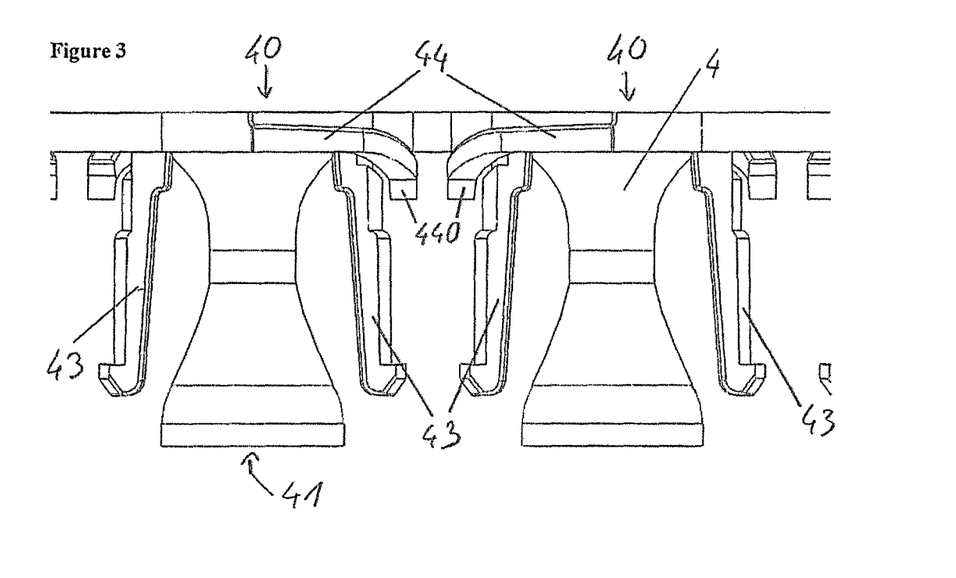
FIG. 3 is a side view of the wells of FIG. 1.

FIGS. 1 to 3 illustrate wells 4 according to a preferred embodiment of the invention. According to this embodiment, the wells 4 are hanging drop wells comprising an inlet 40 and a one drop contact area or culture compartment 41 for adherently receiving a liquid volume for cultivating cells or for producing molecular aggregates therein. The inlet 40 and the culture compartment 41 are connected to each other by a vertical microchannel 42. In an alternative embodiment of the invention the wells have an upper opening and a closed bottom and inner side walls extending from the upper opening to the closed bottom. Usually both openings of this alternative embodiment are of the same shape and size and the well is of cylindrical form. Other type and shapes of wells are however possible within the frame of the invention.

Typically, liquid culture material is loaded into the well 4 with a pipette (not represented) through the inlet 40. The culture material (not represented) deposited in the inlet 40 enters the microchannel 42 and forms a hanging drop (not represented) that adheres to the inner surface of the culture compartment 41. In order to precisely control the quantity of liquid flowing through the microchannel 42 and into the culture compartment 41 for forming the hanging drop, the pipette is preferably placed in direct contact with the inner surface of the inlet 40, as close as possible from the upper opening of the microchannel 42, before a precisely determined volume of culture material is expelled out of the pipette. The wells 4 are preferably automatically loaded, a plurality of wells 4 being for example simultaneously loaded by a series of pipettes.

With reference to FIGS. 2 and 3, the wells 4 comprise fastening elements 43, 44 for attaching them onto a frame (not represented in FIGS. 2 and 3) that holds a plurality of wells 4 in a defined arrangement. According to a preferred embodiment of the invention, at least one of the fastening elements is an elastic element for allowing the wells 4 to be elastically displaceable relative to the frame when attached to the frame.

Each well 4 for example comprises two clips 43, each placed on an opposite side of the well 4 and two springs 44. When the wells 4 are attached to the frame, an adapted portion of the frame is elastically held between the clips 43 and the springs 44. The clips 43 are preferably relatively rigid and are for example connected to the periphery of the inlet 40 of the corresponding well 4. The springs 44 are for example elongated and relatively flexible elements that are also attached to the periphery of the inlet 40 and that are each oriented towards a corresponding clip 43.

In a rest position, the springs 44 for example push on the upper side of the frame while the clips 43 abut against its lower side. When a force is exerted on one or more wells 4, for example during automatic loading of the wells 4 with pipettes, the corresponding springs 44 are for example compressed and the clips 43 slide relative to the frame, thus resulting in an elastic displacement of the corresponding wells 4 relative to the frame. When the force is released, the wells 4 elastically return in their rest position. The fastening elements preferably allow an elastic displacement of the wells in any direction relative to the frame, within a determined range limited by the configuration of the fastening elements, for example by the configuration of the clips and by the springs' stroke in the various directions.

Figure 4:
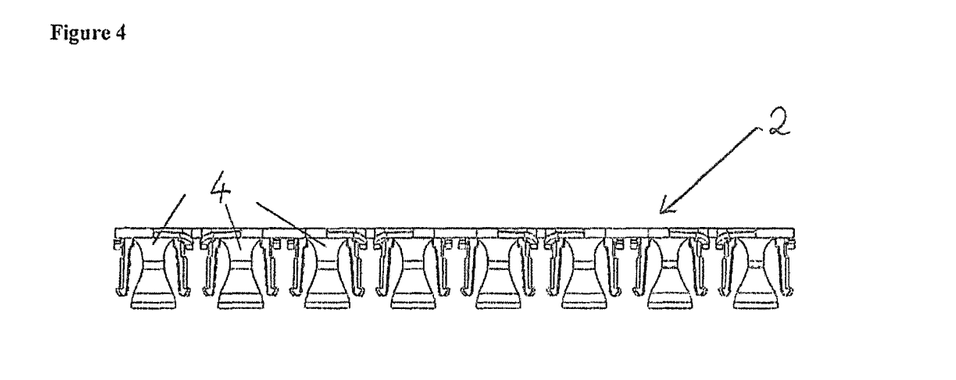
FIG. 4 is a side view of an 8-well stripe with springs and an elastic interconnection element, according to a preferred embodiment of the invention.
Figure 5:
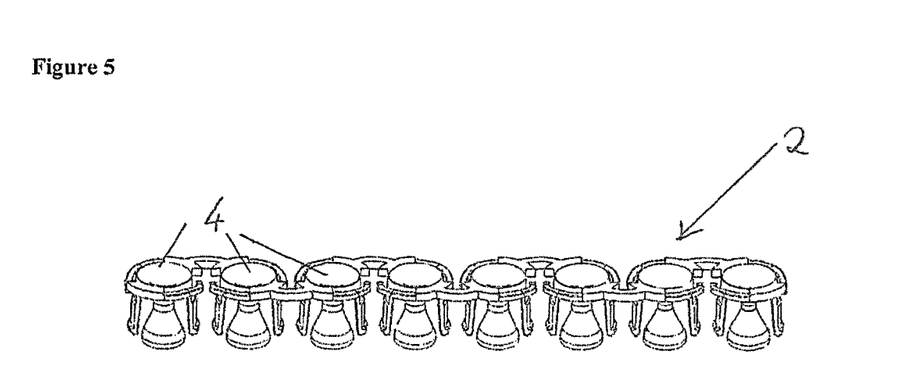
FIG. 5 is a perspective view of the 8-well stripe of FIG. 4.

The wells are manufactured for example in stripes or as matrices or single wells. The wells are preferably manufactured in stripes comprising a given number of wells, wherein at least two neighboring wells 4 are connected to each other for example by a flexible interconnection element 11 allowing for some relative elastic displacement between them. The wells are more preferably manufactured in eight-well stripes. FIGS. 4 and 5 for example illustrate an eight-well stripe 2.

The wells 4 are for example made of a polymeric material. The polymeric material is preferably a biocompatible plastic material such as polycarbonate, polyethylene, polystyrene, polypropylene or polydimethylsiloxan. The wells are for example produced by injection moulding processes using polymeric material, preferably polystyrene or polypropylene, or by casting polymeric materials such as polydimethylsiloxan. Different components of a well 4 can be made from different materials.

According to the preferred embodiment of the invention, the springs 44, and the interconnection elements 11 are integral to the injected stripe 2, but for example with a smaller section than other parts of the stripe 2, which makes them relatively more flexible than these other parts of the stripe 2, in particular more flexible than the clips 43.

According to variant embodiments of the invention, the elastic parts of the fastening elements for elastically attaching the wells to a preferably rigid frame are added to the stripe or to the individual wells after their production. Such elastic parts for example include O-rings and/or elastic inlays that are for example placed between each well and the frame, for example in addition or in replacement of the springs 44 of the embodiment described above.

Figure 6A:
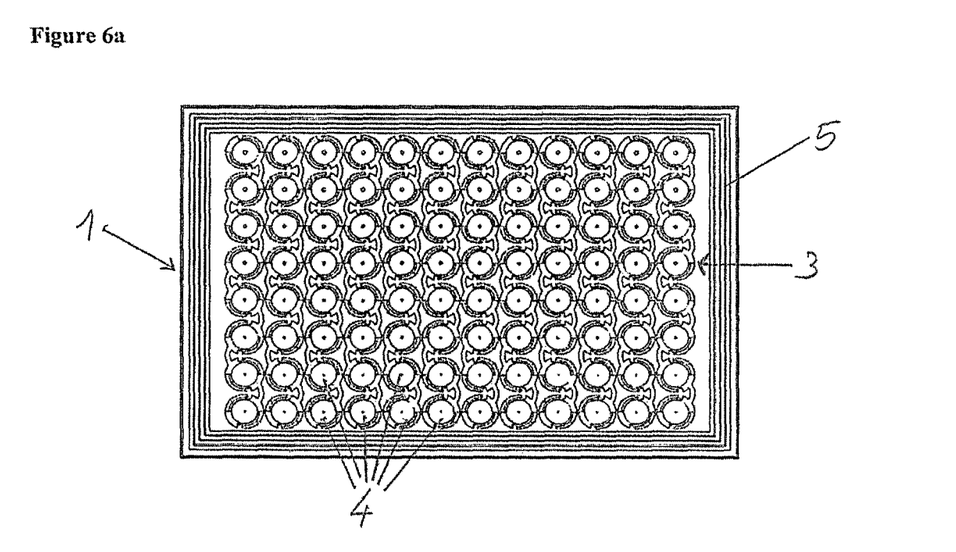
FIG. 6a is a top view of a multi-well plate according to a preferred embodiment of the invention.

FIG. 6a shows an example of a multi-well plate 1 according to a preferred embodiment of the invention. The multi-well plate 1 comprises a frame 5 holding a plurality of wells 4 in a defined arrangement, typically in a two-dimensional arrangement. The wells 4 are preferably distributed in regularly spaced rows and columns within the plane of the frame 5, for example in an 8×12 well matrix 3. Common dimensions for multi-well plates include 8×12 wells (96-well plates) as illustrated for example in FIG. 6a, 16×24 (384-well plates) and 32×48 (1536-well plates). Other dimensions and arrangements are however possible within the frame of the invention.

The frame 5 is preferably made of a rigid material, for example of a rigid plastic, and comprises holes or openings 49 in which the wells 4 are held. According to the preferred embodiment of the invention, the wells 4 are clipped into the corresponding holes or openings 49 and elastically held to the plate between their clips 43 and springs 44.

The frame 5 is for example made of a polymeric material, preferably a biocompatible plastic material such as polycarbonate, polyethylene, polystyrene or polypropylene, more preferably polycarbonate, and is preferably prepared in a single piece by injection moulding.

Figure 6B:
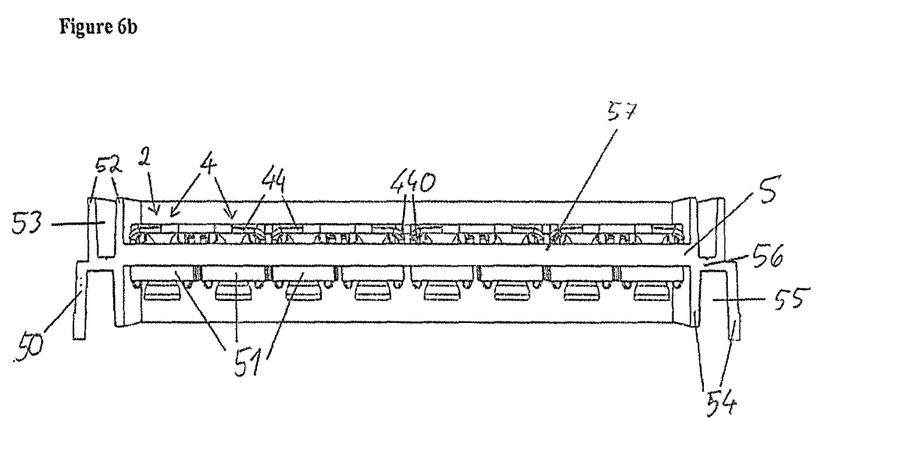
Figure 7:
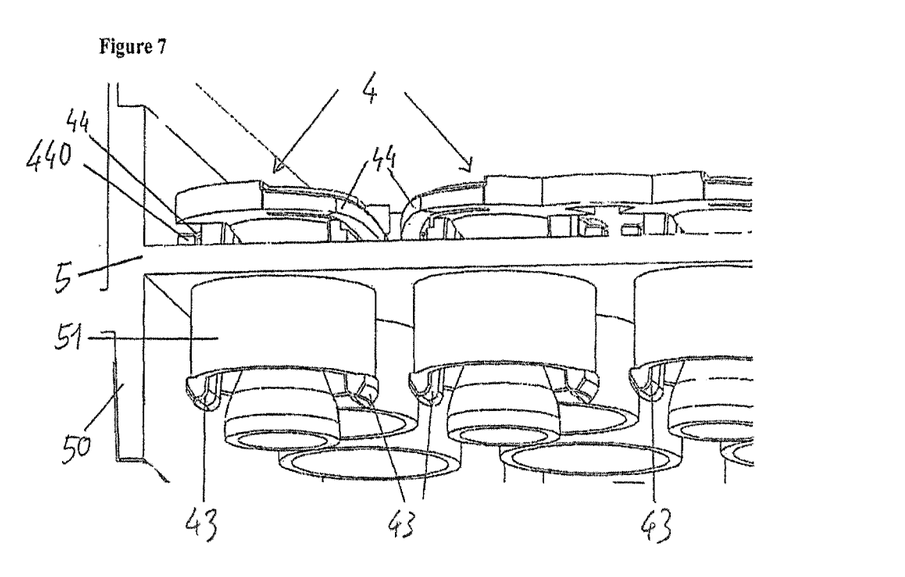
FIG. 7 is a perspective view of a detail of the cut view of FIG. 6b.

With reference to FIGS. 6b and 7 showing a cut view of the culture plate of FIG. 6a with only one stripe 2 of wells 4, the frame 5 comprises openings configured for cooperating with the fastening elements of the wells 4 for attaching them to the frame 5, each opening being preferably configured for receiving one well 4. The openings for example comprise elongated cylindrical walls 51 extending below the surface 57 of the frame 5.

The frame 5 further preferably comprises upper side walls 52 extending above the surface 57 of the frame 5 around the periphery of the frame 5, defining an upper ridge or channel 53 there between, lower side walls 54 extending below the surface 57 of the frame 5 around the periphery of the frame 5, defining a lower ridge or channel 55 there between, the upper ridge or channel 53 and the lower ridge or channel 55 being preferably separated by a wall 56.

According to the invention, the frame 5 further comprises a support element 50 for contacting a surface 6, for example a work surface or a loading station of an automatic loading machine, when the multi-well plate 1 is placed on said surface 6. The support element 50 is for example attached to or part of one of the lower side walls 54.

According to the preferred embodiment illustrated in FIG. 7, each opening comprises an elongated cylindrical wall 51 extending below the surface 57 of the frame 5. When a well 4 is attached to the frame in the corresponding opening, the cylindrical wall 51 is clipped between the clips 43 on one side and the lower part 440 of the corresponding springs 44 on the other side. Each well 4 is thus elastically attached to the frame 5.

Other configurations of the fastening elements, in particular of their elastic parts, and/or the openings are however possible within the frame of the invention in order to allow an elastic displacement of the wells relative to the frame when the wells are attached to the frame.

Figure 8:
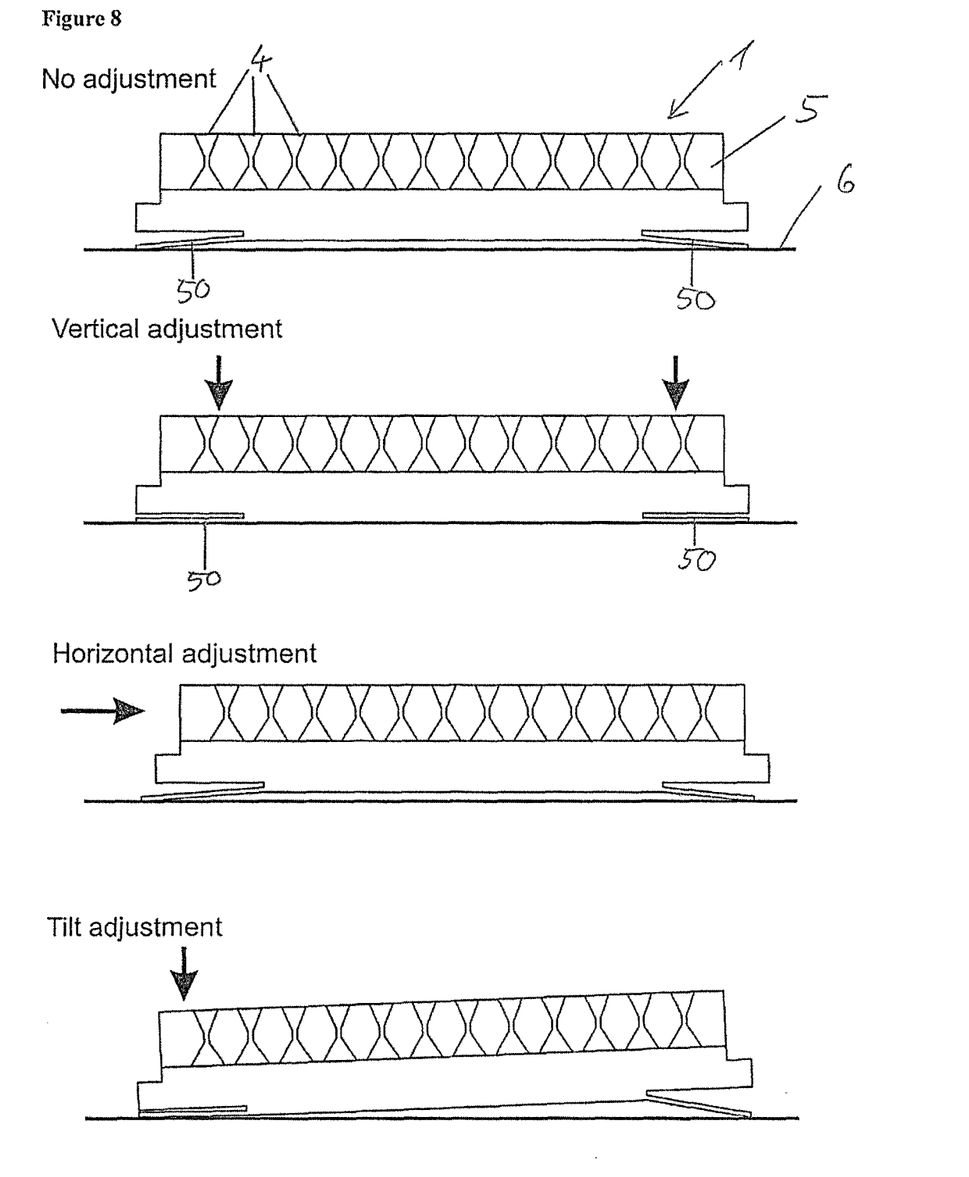
FIG. 8 schematically illustrates a multi-well plate according to another embodiment of the invention in different position adjustment situations.
Figure 9:
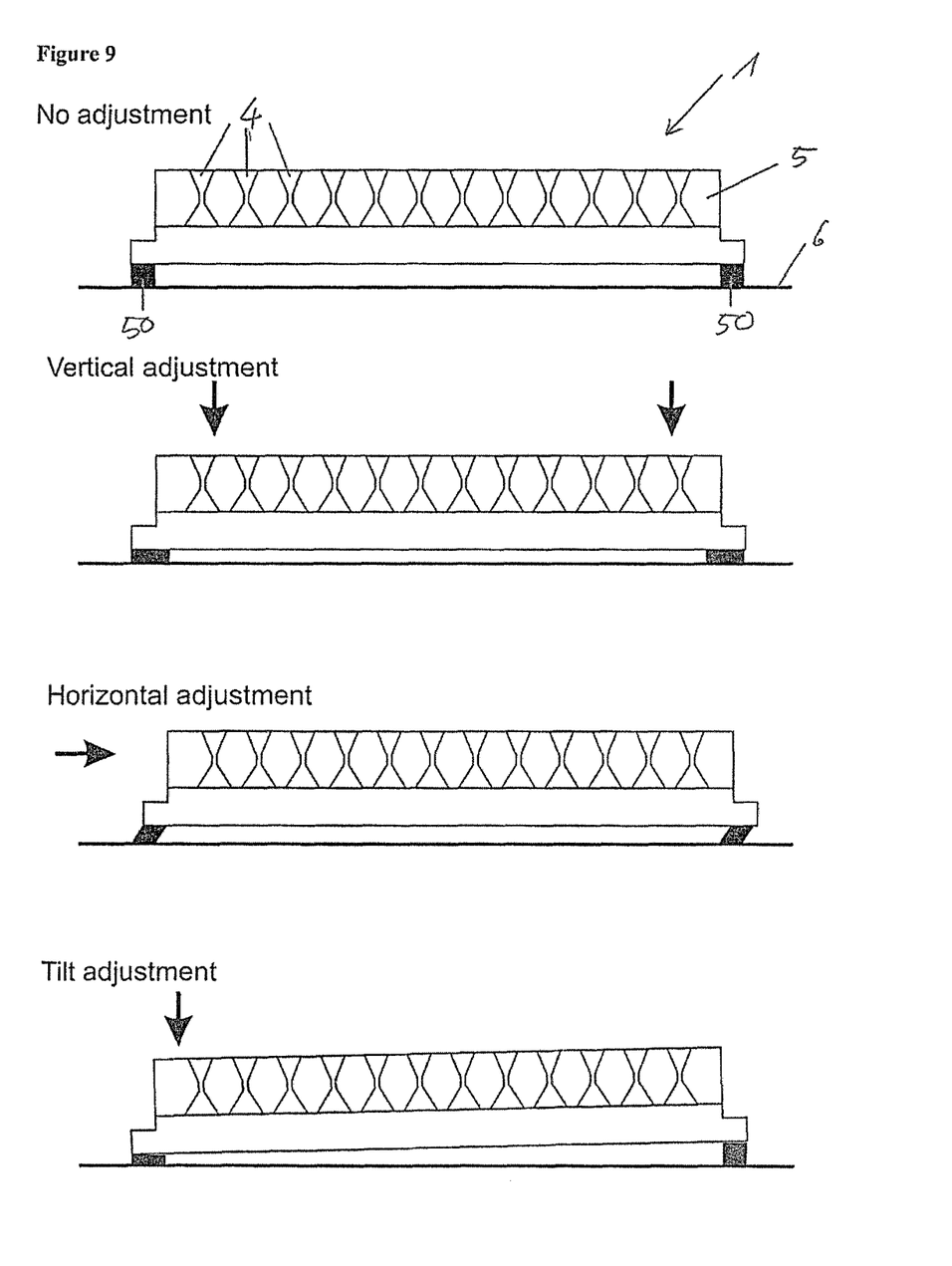
FIG. 9 schematically illustrates a multi-well plate according to still another embodiment of the invention in different position adjustment situations.

FIGS. 8 and 9 schematically illustrate other embodiments of the invention, in which the frame 5 supporting the wells 4 comprises an elastic support element 50.

According to the embodiment illustrated in FIG. 8, the support element 50 at the lower part of the frame 5 comprises flexible tongues that contact a surface 6 on which the multi-well plate 1 is placed. The flexible tongues are for example elongated and relatively thin elements that are placed for example at the periphery of the frame 5. Preferably, the tongues are made of the same material as the frame 5 and the frame with the support element 50 are for example moulded together as a single piece. The wells 4 are preferably attached to the frame 5, either as single wells or in stripes, matrices or other subsets of wells.

In a rest position (no adjustment), the tongues of the support element 50 slightly lift the frame 5 above the surface 6.

If a vertical force is regularly applied on the multi-well plate 1 of the invention, for example during automatic loading of the wells 4 with pipettes, the support element 50 is compressed and the frame 5 with the wells 4 comes closer too the surface 6 (vertical adjustment).

If a lateral force is applied on the multi-well plate 1 of the invention, for example due to a misalignment of the pipette relative to the wells 4 during automatic loading of the wells 4, the support element 50, in particular the tongues, stretches on one side of the plate and is compressed on the other side, such that the frame 5 and thus the wells 4 are elastically displaced relative to the support element 50 and thus relative to the surface 6 (horizontal adjustment).

Similarly, if a vertical force is applied on one side of the multi-well plate 1 of the invention, the support element 50 is compressed on this side and stretches on the other side of the plate 1. The orientation of the plane of the frame 5, and thus of the wells 4, relative to the support element 50 and thus relative to the surface 6 is then elastically modified (tilt adjustment).

FIG. 8 illustrates the exaggerated elastic displacement of the frame 5 relative to the support element 50 under the effect of different schemes of external forces. A combination of the illustrated forces is however possible, thus resulting in a corresponding combination of the illustrated displacements.

FIG. 9 illustrates another example of a multi-well plate 1 of the invention with an elastic support element 50. The support element 50 is made for example of one or more pieces of a flexible material, attached, for example glued, or co-moulded during the injection-molding process under the frame 5, preferably at its periphery. According to this variant, the frame 5 and the support element 50 are preferably manufactured separately and the support element 50 is attached to the frame 5 at a later stage. However, co-injection moulding could be used, too.

As illustrated in FIG. 9, the multi-well plate 1 according to this variant behaves similarly to that illustrated in FIG. 8 when submitted to similar external forces, resulting in elastic displacement of the frame 5 relative to the support element 50.

Figure 9A:
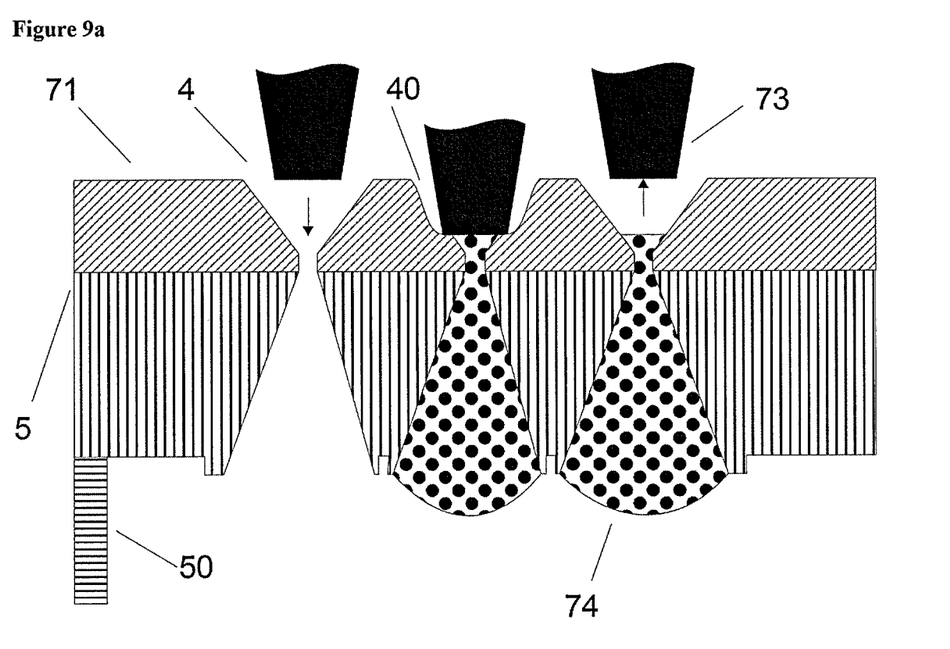
FIG. 9a schematically illustrates a multi-well plate according to still another embodiment of the invention with an elastic layer providing the compliance of the inlets.

FIG. 9a illustrates another example of a multi-well plate 1 of the invention with an elastic layer 71 that forms together with the frame 5 the well 4 comprising elastic inlets 40. The elastic layer 71 is made for example of one or more pieces of a flexible material, such as e.g. polydimethylsiloxane, silicone or other rubber-like materials. attached, for example glued, physically bonded or co-moulded during the injection-molding process onto the frame 5. According to this variant, the frame 5 and the elastic layer 71 are preferably manufactured separately and the elastic layer 71 is attached to the frame 5 at a later stage. However, co-injection moulding could be used, too. In this embodiment the frame 5 remains static, while the compliance needed to assure a good seal between the pipette tip 73 and the inlets 40 is generated by an elastic deformation of the inlet 40 of the elastic layer 71 by the pipette tip 73.

According to the embodiment of the invention illustrated by the examples of FIGS. 8, 9 and 9a, the wells 4 are for example directly formed in the frame 5, or firmly attached to the frame 5, so they are not displaceable relative to the frame 5 when they are attached to it, or they are elastically attached to the frame 5, so they are displaceable relative to the frame 5 when they are attached to it. The wells 4 are attached to the frame 5 either as single wells, stripes of wells or matrices of wells. The elastic layer 71 is attached to the frame 5 either as stripes or matrices of wells.

Figure 10:
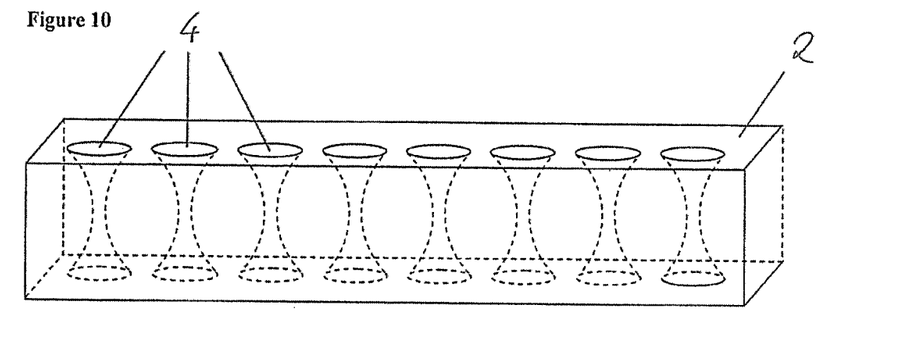
FIG. 10 is a perspective view of wells casted in a flexible material, according to another embodiment of the invention.
Figure 11:
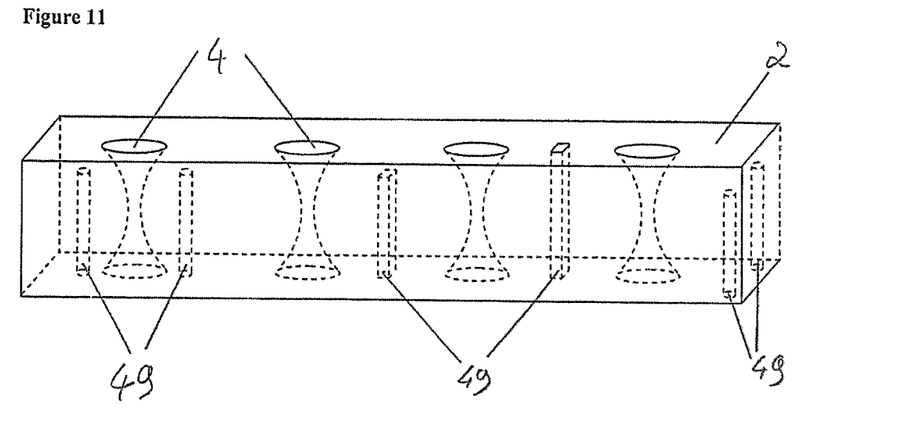
FIG. 11 shows a variant embodiment of the wells of FIG. 10 with cut outs to be fixated onto a rigid support.

FIGS. 10 and 11 illustrate another embodiment of the invention wherein the wells 4 are formed, for example as a stripe 2, in a bloc of a flexible material, which is then attached to a frame (not represented). The bloc and the openings forming the stripe 2 of wells 4 are for example moulded as a single piece of a flexible biocompatible material. According to this embodiment, the wells 4 are flexible and displaceable relative to each other and/or relative to the frame on which the stripe 2 is attached, and thus relative to the support element of the frame.

The example illustrated in FIG. 11 additionally comprises further openings 49 for attaching it to the frame and/or for improving the flexibility of the material and thus increasing the amplitude of the possible displacement of the wells 4 relative to each other. Other structure of the stripe forming bloc are possible within the frame of the invention in order to optimize its flexibility.

In the illustrated examples, the wells are formed in stripes 2. The wells 4 can however be manufactured as single wells individually attached to the frame, as stripes of wells or as matrices of wells, or as any other subset of wells.

According to the invention, the wells 4 and/or the frame 5 are elastically supported and are thereby elastically displaceable, preferably in any direction, relative to the support element 50 of the culture plate 1, which contacts the surface on which the multi-well plate 1 is placed. The wells 4 are thus elastically displaceable in a direction perpendicular to the plane of the frame 5 and/or in a direction parallel to the plane of the frame 5 relative to the support element 50, and thus relative to the surface 6 on which the multi-well plate 1 is placed.

The compliance of at least one well 4 in a direction perpendicular to the plane of the frame 5 is preferably between 0.1 mm and 2 mm, more preferably between 0.1 mm and 1 mm. The compliance of at least one well 4 in a direction parallel to the plane of the frame 5 is preferably between 0.1 mm and 1 mm, more preferably between 0.1 mm and 0.5 mm.

The possible displacement of the wells 4 relative to the support element 50 and thus relative to the surface on which the multi-well plate 1 is placed, allows for an improved loading, or pipetting, of the wells 4, in particular in case of automatic loading of hanging drop wells, where a precise contact between the pipettes and the inlet of the wells 4 is of great importance. Indeed, the possible displacement of the wells 4 relative to the support element 50, either individually, in stripe or in matrices, allows for a correction of possible vertical and/or horizontal misalignments between the pipettes and the wells 4.

Figure 12:
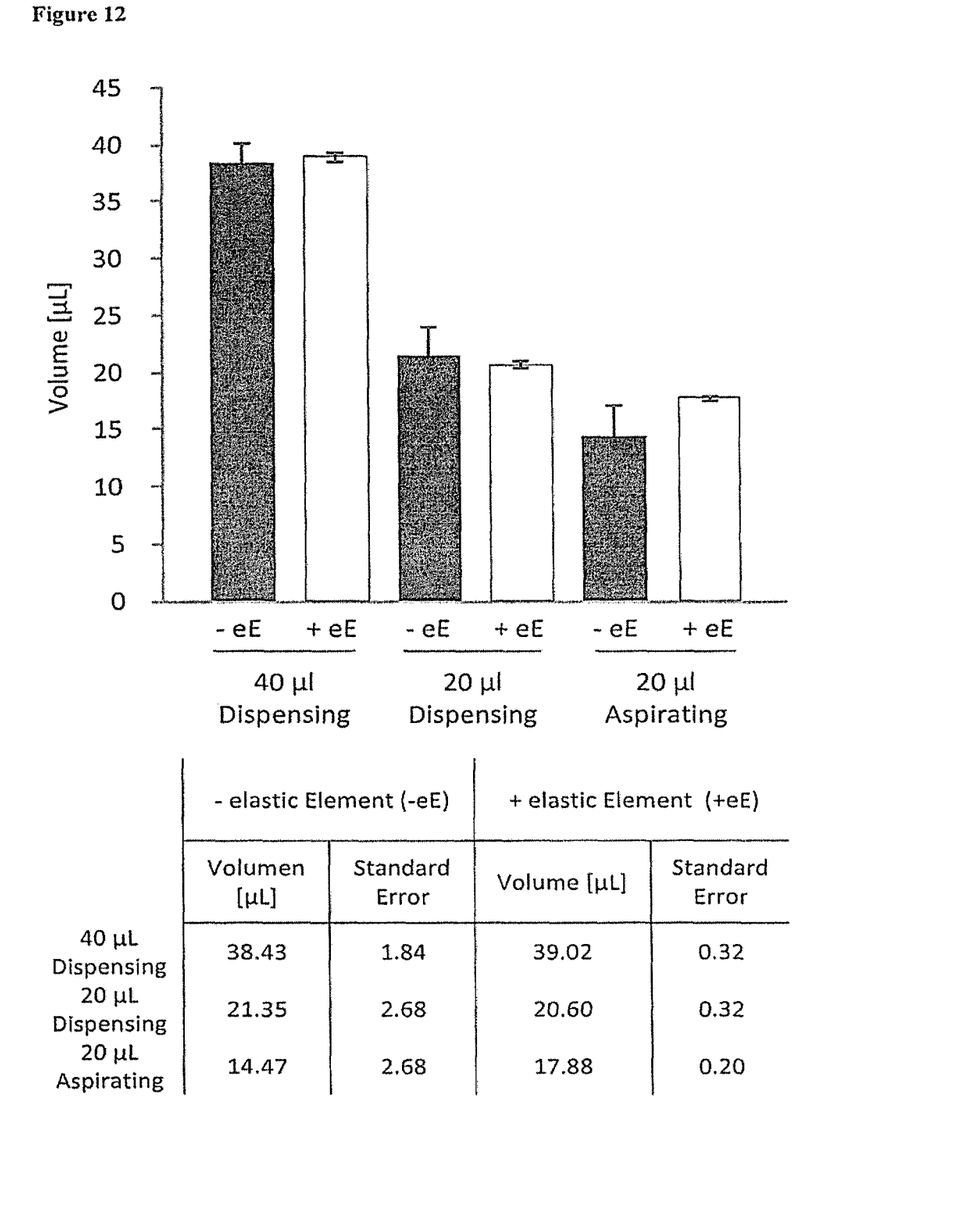
FIG. 12 shows the improved pipetting accuracy using hanging drop wells according to the invention compared to using prior art hanging drop wells.

FIG. 12 illustrates the results of corresponding experiments showing the improved pipetting accuracy comparing hanging drop wells without elastic elements −eE and hanging drop wells according to the invention with elastic elements +eE.

Figure 13:
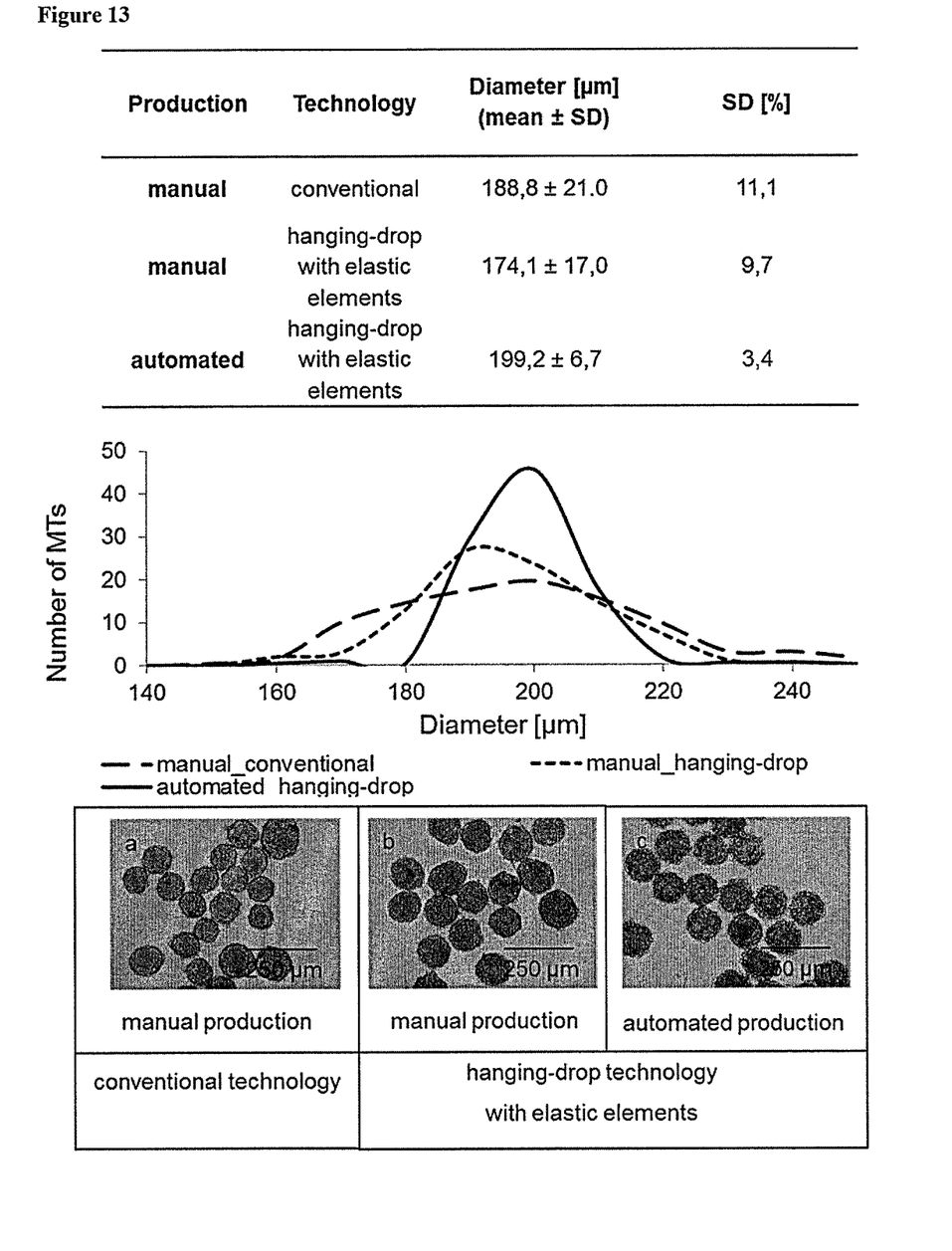
FIG. 13 shows the improved pipetting accuracy using hanging drop wells according to the invention with an automatic, parallel pipetting system compared to two manual pipetting modes.

FIG. 13 illustrates that an automated, parallel pipetting approach, using elastic elements, improves the production precision of cell aggregates in terms of their size.

Figure 14:
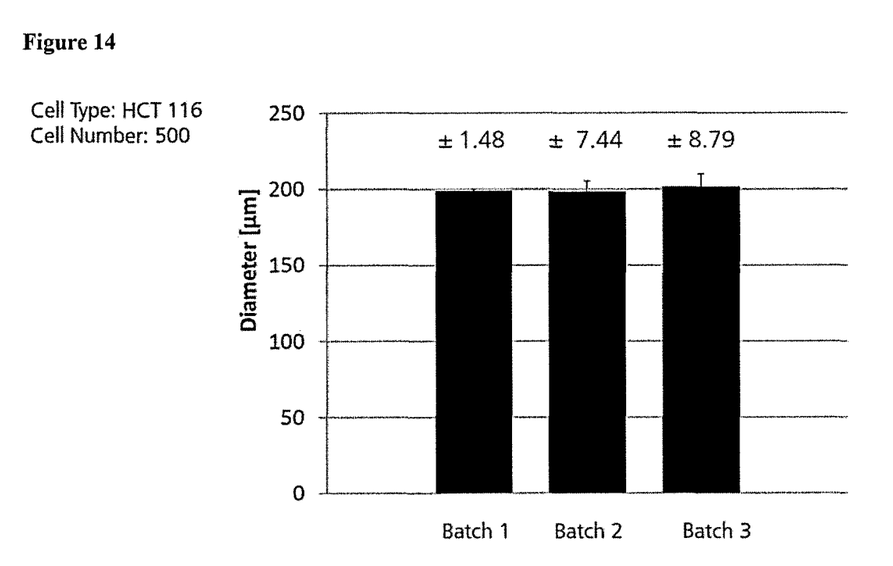
FIG. 14 shows the low batch-to-batch variation of the size of cell aggregates formed in a compliant microwell plate.

FIG. 14 shows that the low size variation using elastic elements is also resulting in low batch-to-batch variations.

EXAMPLES

Example 1

Improved Pipetting Accuracy Comparing Hanging Drop Wells without Elastic Elements (−eE) and with Elastic Elements (+eE)

The data as shown in FIG. 12 was acquired using a liquid handling robotic system (Nimbus, Hamilton, Switzerland). A 96-well matrix comprised of 12 individual 8-well stripes of hanging drop wells as illustrated in FIGS. 4 and 5 attached to a holding frame were used. Volumes of 40 and 20 μl of standard cell culture medium supplemented with 10% fetal calf serum were placed into the hanging drop wells and the total weight measured (n=10). Moreover, to simulate medium sampling of the individual hanging drop wells, 20 μl cell culture medium was aspirated using a 96-well pipette head and the total volume measured (n=10).

Example 2

Improved Precision of Production of Cell Aggregates in Plates with Elastic Elements Using Automatic, Parallel Liquid Handling An important advantage of the elastic elements of the compliant multiwell plate is that automated, parallel liquid handling technologies can be used. The compliance in the elements assures a tight sealing between the parallel pipette tips and the plate, resulting in highly reliable liquid dispensing and aspiration (as can be seen in Example 1). When producing biological cell aggregates in such a system, a defined volume of cell-culture medium with a defined cell concentration is dispensed into the plate. The number of cells introduced into the system is therefore directly proportional to the volume.

The data in FIG. 13 illustrates that the use of automated, parallel liquid handling systems in conjunction with the compliant multiwell plate and its elastic elements as described in Example 1 with a 96-well matrix comprised of 12 individual 8-well stripes of hanging drop wells as illustrated in FIGS. 4 and 5 made of polystyrene attached to a holding frame made of polystyrene results in a highly reproducible production on cell aggregates (microtissues, MT). Microtissues where formed from 500 HCT-116 cells, dispensed into a hanging drop using manual and automated, parallel pipetting systems. The first fabrication approach uses manual, sequential pipetting onto a solid surface, which subsequently turned to obtain hanging drops. The second approach uses manual, sequential pipetting into a cell culture plate with elastic elements. The third approach uses an automated, parallel pipetting technology and the cell culture plate with elastic elements.

After the formation of cell aggregates, the diameter of 96 aggregates for each production approach was determined using a calibrated microscope. The table in FIG. 13 shows the mean diameter and standard deviation for each of the three production approaches. The automated approach (solid line in the diagram) results in a standard deviation of 3.4%, while the two fabrication approaches using a manual, sequential pipetting result in 9.7% and 11% std. dev.

Example 3

Low Standard Deviation and Low Batch-to-Batch Variation of Cell Aggregates Formed in the Multiwell Plate with Elastic Elements Expanding on the previous examples, the data shown in FIG. 14 illustrates the low batch-to-batch variations of cell-aggregate size of microtissues produced in the multiwell plate with elastic elements. The data was acquired using a liquid handling robotic system (Nimbus, Hamilton, Switzerland) to form cell aggregates from an HCT-116 cancer cell line starting with 500 cells. Three completely independent fabrication runs were made using the multiwell plate with elastic elements according to Example 2. For each run, a new cell suspension was prepared to obtain completely independent batch-to-batch information. Again, the cell diameter was obtained from measuring 96 cell aggregates under a calibrated microscope. The resulting batch-to-batch variations are below 5% for three cases (the variations denoted on the graph are in μm).

REFERENCE NUMBER LIST 1 multi-well plate
11 interconnection element
2 8-well stripe
3 8×12 well matrix
4 well
40 inlet
41 culture compartment
42 microchannel
43 clip
44 spring
440 lower part
49 opening
5 frame
50 support element
51 cylindrical walls
52 upper side wall
53 upper ridge or channel
54 lower side wall
55 lower ridge or channel
56 wall separating the upper and lower ridges or channels
57 surface of the frame 5
6 surface
71 elastic layer
73 pipette tip
74 hanging drop

The invention claimed is:
1. A multi-well plate (1) comprising:
a plurality of wells (4);
a frame (5) holding said plurality of wells (4) in a defined arrangement;

an elastic element connecting the plurality of wells (4) to said frame (5) or a surface (6); or an elastic support (50) for contacting a surface (6) when said multi-well plate (1) is placed on said surface (6), wherein each well (4) of said plurality of wells (4) is elastically displaceable relative to said surface (6) and wherein each well (4) of said plurality of wells (4) is a hanging drop well comprising an inlet (40) and a culture compartment (41) for adherently receiving a liquid volume for cultivating cells or for producing molecular aggregates therein, and wherein the inlet (40) and the culture compartment (41) are connected to each other by a vertical microchannel (42), wherein said elastic element is selected from at least one of a clip (43) or a spring (44), and wherein said elastic support is selected from at least one of a flexible tongue or a flexible piece of material attached under said frame (5).

2. Multi-well plate according to claim 1, wherein said plurality of wells (4) is elastically displaceably relative to said frame (5).

3. Multi-well plate according to claim 2, wherein said plurality of wells (4) is elastically displaceable in a direction perpendicular to the plane of said frame (5) of between 0.1 and 2 mm, and in a direction parallel to the plane of said frame (5) of between 0.1 and 1 mm.

4. Multi-well plate according to claim 1, wherein said at least one well (4) is elastically supported on said frame (5).

5. Multi-well plate according to claim 1, wherein said plurality of wells (4) is part of a subset of wells and said subset of wells is elastically supported on said frame (5).

6. Multi-well plate (1) according to claim 5, wherein at least two neighboring wells (4) of said subset of wells are elastically interconnected.

7. Multi-well plate (1) according to claim 1, wherein the frame (5) comprises openings (49) with cylindrical walls (51) extending below a surface (57) of the frame (5), for holding at least one well (4) of said plurality of wells (4).

8. Multi-well plate (1) according to claim 7, wherein said openings (49) are arranged in an array of 8×12, of 16×24 or of 32×48 holes.

9. Multi-well plate (1) according to claim 1, wherein said frame (5) is elastically displaceable relative to said support (50).

10. Multi-well plate according to claim 9, wherein said frame (5) is elastically displaceable relative to said support (50) in a direction perpendicular to the plane of said frame (5) of between 0.1 and 2 mm, and in a direction parallel to the plane of said frame (5) of between 0.1 and 1 mm.

11. Multi-well plate (1) according to claim 1, wherein said frame (5) is elastically supported by said support (50).

12. Multi-well plate (1) according to claim 1, wherein at least a subset of said plurality of wells (4) is formed in a bloc of a flexible material.

13. Multi-well plate (1) according to claim 12, wherein said bloc of flexible material is supported by a rigid structure.

14. Multi-well plate (1) according to claim 12, wherein said bloc of flexible material comprises an elastic layer (71) that forms together with the frame (5) the subset of said plurality of wells (4).

* * * * *